United States Patent [19]

Wiegand et al.

[11] Patent Number: 4,954,448
[45] Date of Patent: Sep. 4, 1990

[54] MODULATION OF ADENYLATE CYCLASE RESPONSE

[75] Inventors: Karl E. Wiegand, Baton Rouge, La.; Robert K. Rude, Los Angeles, Calif.

[73] Assignee: Nelson Research & Development Company, Irvine, Calif.

[21] Appl. No.: 290,307

[22] Filed: Dec. 27, 1988

[51] Int. Cl.$^5$ ............................................. C12N 9/88
[52] U.S. Cl. ................................... 435/232; 424/600; 424/722; 424/724; 435/184
[58] Field of Search ................. 435/189, 232; 424/600, 424/722, 724

[56] References Cited

PUBLICATIONS

Carlisle, "Silicon: A Requirement of Bone Formation Independent of Vitamin D" (1981) *Calcif. Tissue Int.* 33, 27–34.
Rude, "Skeletal Adenylate Cyclase: Effect of $Mg^{+2}$, $Ca^{2+}$ and PTH" (1985) *Calcif. Tissue Int.* 37:318–323.
Rude, "Renal Cortical Adenylate Cyclase Characterization of Magnesium Activation" (1983) *Endocrinology*, vol. 113, No. 4, 1348–1355.
Carlisle, "Silicon: An Essential Element for the Chick" (1972) *Science*, vol. 178, 619.
Carlisle "Silicon: A Possible Factor in Bond Calcification" (1970) *Science*, vol. 167, 279.
Cech et al., "Adenylate Cyclase: The Role of Magnesium and Other Divalent Cations" (1980) *Molecular and Cellular Biochemistry*, 33, 67 92.

*Primary Examiner*—Robert A. Wax
*Attorney, Agent, or Firm*—Robert J. Baran; Walter A. Hackler

[57] ABSTRACT

Silicic acid modulates (i.e. enhances or inhibits) adenylate cycloase activity. This effect appears to be a general one, inasmuch as the modulation has occurred in all tissues studied. The results suggest that silicic acid can be used in human and veterinary medicine to modulate hormone or neurotransmitter response. The results also indicate that silicic acid can be used to prevent, treat, or delay the onset of calcium-related bone disease, or to improve bone strength in an vertebrate having a bone strength less than desired.

7 Claims, 5 Drawing Sheets

MODULATION OF ADENYLATE CYCLASE RESPONSE

FIELD OF THE INVENTION

This invention relates to adenylate cyclase systems, and their stimulation or inhibition with a silicic acid, i.e. monosilicic acid or a closely-related molecular species. It has been discovered that silicic acid modulates both basal and hormone-stimulated adenylate cyclase activity.

BACKGROUND OF THE INVENTION

The responsiveness of many cells to external chemical messengers, such as hormones, lymphokines, growth factors, neurotransmitters, and the like, is elicited by way of receptors to these substances. A large variety of these receptors are coupled with an enzyme system, adenylate cyclase, which catalyzes the conversion of adenosine triphosphate (ATP) to cyclic adenosine monophosphate (cyclic AMP, or cAMP for short) and pyrophosphate. Cyclic AMP release inside a cell causes activation of other enzymes, resulting ultimately in the biological response. An important approach in the treatment of disease, or control of physiological states, is the ability to modify the responsiveness of cells to these messengers. By so doing, it may be possible to modify a number of conditions by a generic mechanism. In the discovery embodied within the invention disclosed and claimed herein, all cyclic AMP systems so far tested respond to silicate treatment.

It is estimated that 20 million people in the U.S. have osteoporosis, which results in 1.3 million fractures annually at a cost of $6.1 billion; Riggs, L. B. and Melton, L. J. III: Involutional Osteoporosis. *N. Engl. J. Med.* 26:1676–1684, 1986. The major contributing factors to osteoporosis is age-related bone mineral loss and estrogen deficiency due to natural menopause; Concensus Conference: Osteoporosis, *JAMA* 252:799–802, 1984; Avioli, L. V.: Osteoporosis: Pathogenesis and Therapy, in: *Metabolic Bone Disease*, Aviolo, L. V. and Krane, S. M. (eds), Academic Press, New York Vol I, pp 307–385, 1977. The mechanism by which this loss is incurred is unclear.

Cyclic AMP has been identified as a mediator of action of PTH as well as other hormones such as calcitonin on bone; Chase, L. R. and Aurbach, G. D.: The Effect of Parathyroid Hormone on The Concentrations of Adenosine 3″,5″-Monophosphate In Skeletal Tissue *in vitro*, *J. Biol. Chem.* 245:1520–1526, 1970; Luben, R. A., Wong, G. L. and Cohn, D. V.: Biochemical Characterization with Parathormone and Calcitonin of Isolated Bone Cells: Provisional Identification Of Osteoclasts And Osteoblasts, *Endocrinology* 99:526–534, 1976; Peck, W. A., Burks, J. K., Wilkins, J., Rodan, S. B. and Rodan, G. A.: Evidence for Preferential Effects of Parathyroid Hormone, Calcitonin And Adenosine On Bone and Periosteum, *Endocrinology* 100:1357–1364, 1977; Rodan, G. A. and Martin, T. J.: Role of Osteoblasts In Hormonal Control Of Bone Resorption—A Hypothesis, *Calcif. Tissue, Int.*, 33:349–351, 1981. The enzyme responsible for the generation of cyclic AMP, adenylate cyclase, is a protein complex consisting of three components: the hormone-specific receptor, the guanine nucleotide regulatory proteins (Ns and Ni), and the catalytic unit; Ross, E. M. and Gilman, A. G.: Biochemical Properties Of Hormone Sensitive Adenylate Cyclase, *Annu. Rev. Biochem.* 49:533–564, 1980. Stimulation of adenylate cyclase activity resulting from hormone binding to a specific receptor is brought about via activation of the stimulatory guanine nucleotide regulatory protein Ns; inhibition of adenylate cyclase activity resulting from activation of the inhibitory guanine nucleotide regulatory protein, Ni; Smigel, M., Katada, T., Northup, J. K., Bokoch, G. M., Ui, M. and Gilman, A.G.: Mechanism of Guanine Nucleotide-Mediated Regulation Of Adenylate Cyclase Activity, in: *Advances in Cyclic Nucleotide and Protein Phosohorylation Research;* Greengard, P. (ed) Raven Press, New York, 17:1–18, 1984; Cote, T. E., Frey, E. A. and Sekura, R. D.: Altered Activity Of The Inhibitory Guanyl Nucleotide-Binding Component (Ni) Induced By Pertussin Toxin, *J. Biol. Chem.* 259:8693–8698, 1984. The overall adenylate cyclase activity expressed in a given system seems to reflect the relative proportion of activated Ns and Ni present. The activation of the adenylate cyclase-cyclic AMP system involves the coordinated interaction of the structural components of the enzyme complex in the presence of guanine nucleotides and $Mg^{++}$; Iyengar, R. and Birnbaumer, L.: Hysteric Activation Of Adenylyl Cyclases: I. Effect of Mg Ion On The Rate Of Activation By Guanine Nucleotides And Fluoride, *J. Biol. Chem.* 256:11036–11041. Most hormones have been shown to increase the magnesium affinity of adenylate cyclase; Iyengar, R. and Birnbaumer, L.: Hormone Receptor Modulates The Regulatory Component Of Adenylyl Cyclase By Reducing Its Requirement for $Mg^{++}$ And Enhancing Its Extent Of Activation By Guanine Nucleotides, *Proc. Natl. Acad. Sci. (USA)* 79:5179–5183, 1982; Cech, S. V., Broaddus, W. C. and Maguire, M. E.: Adenylate Cyclase: The Role of Magnesium And Other Divalent Cations, *Mol. Cell. Biochem.* 33:67–92, 1980, and it has been suggested that the mechanism of hormonal activation involves an increase in $Mg^{++}$ affinity of the adenylate cyclase complex.

Calcium also has been shown to influence adenylate cyclase activity. Inhibition of adenylate cyclase by $Ca^{++}$ at concentrations of 0.01–1.0 mM appears to be a general property of all adenylate cyclase enzymes; Cech, S. V., Broaddus, W. C. and Maguire, M. E.: Adenylate Cyclase: The Role Of Magnesium And Other Divalent Cations, *Mol. Cell. Biochem.* 33:67–92, 1980. A previous investigation of the effects of $Ca^{++}$ on the adenylate cyclase activity in guinea pig bone revealed the presence of two calcium inhibition sites with calcium disassociation constants or approximately 1 micromole and 200 micromole; Rude, R. K.: Renal Cortical Adenylate Cyclase: Characterization Of Magnesium Activation, *Endocrinology* 113:1348–1355, 1983; Rude, R. K.: Skeletal Adenylate Cyclase: Effect Of $Mg^{2+}$, $Ca^{2+}$, and PTH, *Calcif. Tissue. Int.* 37:318–323, 1985. The high affinity calcium inhibition site is likely to play a physiological role in the regulation of bone adenylate cyclase.

Silicon has been demonstrated to be an essential trace element; Carlisle, E. M.: Silicon as an Essential Element, *Fed. Proc.* 33:1758–1766, 1974; Carlisle, E. M.: Silicon As An Essential Trace In Animal Nutrition, in: *Silicon Biochemistry*, Wiley, Chichester (Ciba Foundation Symposium 121), pp. 123–139, 1986. In biological tissues the highest levels of silicon are found in connective tissues. Silicon deficiency in the chick has been shown to impair normal skeletal development; Carlisle, E. M.: Silicon: An Essential Element For The Chick, Science, 178:619–621, 1972. Silicon appears to be necessary in areas of active bone growth and/or mineralization; Carlisle, E. M.: Silicon: An Essential Element for the chick, ibid.; Carlisle, E. M.: Silicon: A possible factor in bone calcification, Science, 167: 280, 1970. These effects are independent of vitamin D; Carlisle, E. M.: Silicon: A Requirement In Bone Formation Independent Of Vitamin D. Calcif. Tissue Int. 33:27–34, 1981.

Preliminary data from other investigators indicate that silicon compounds can increase bone mass. It has been proposed that silicon compounds may be beneficial in the treatment of osteoporosis; European Patent Application No. 86-116363.2.

SUMMARY OF THE INVENTION

Silicic acid will modify basal and hormone-stimulated adenylate cyclase activity. This effect appears to be a general one in as much as this augmentation has occurred in all tissues studied.

The mechanism(s) responsible for this effect is (are) unclear. The lack of effect of silicic acid in the presence of ethylene glycol—0,0'-bis(2-aminoethyl)-N,N,N',N' tetraacetic acid (EGTA) suggests that silicic acid may merely be acting via binding ionized $Ca^{++}$ and thereby increasing adenylate cyclase activity by removing the inhibitory action of $Ca^{++}$. Since $Ca^{++}$ is an important intracellular second messenger and silicic acid has been found within the cell, this is a possible mechanism of the effect of silicic acid in vivo. However, experimental results indicate that more is involved. Silicic acid could also bind $Mg^{++}$ and cause a reduction in adenylate cyclase activity. This could explain the finding with kidney and/or liver adenylate cyclase systems (set forth below) where $Ca^{++}$ was low (0.2 micromole) and silicic acid caused inhibition of activity. However, monosilicic acid is a very weak acid, it is thought to only interact with metal ions at pH levels just below the level at which hydroxide precipitation occurs which would tend to exclude $Ca^{++}$ and $Mg^{++}$ at a physiological pH.

Other potential mechanisms also exist. Monosilicic may either influence $Mg^{++}$ activation or $Ca^{++}$ inhibition of N protein(s) or the affinity of these divalent cations for the N protein. Additionally, silicic acid could directly cause activation of Ns or inhibition of Ni activity. Other potential mechanisms include a decrease in K-activation by hormone or direct enhancement of catalytic subunit activity.

The clinical significance of these findings remain to be elucidated. Silicon deficiency impairs normal skeletal development in the chick and supplemental silicon enhances bone growth. It is conceivable that these effects may be mediated via the adenylate cyclase-cyclic AMP system. The fact that silicon is found in highest amounts in connective tissues probably accounts for the prominent effect on bone rather than soft tissue. The importance of the potential usefulness of silicic acid in the treatment of osteoporosis is apparent.

DESCRIPTION OF PREFERRED EMBODIMENTS

Figure 1:
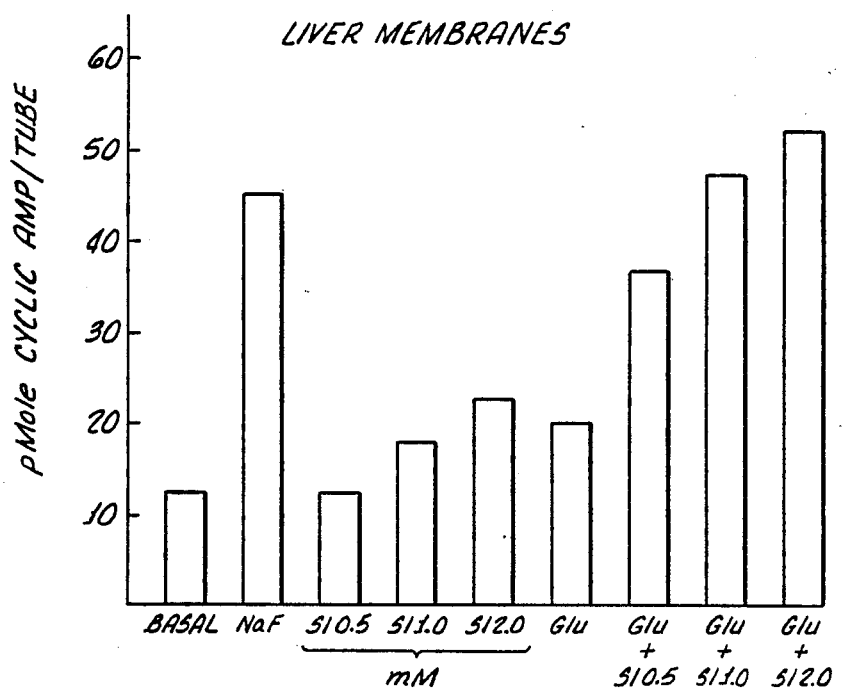
FIG. 1: Effect of NaF, 0.5, 1.0 and 2.0 mM Si, glucagon, and glucagon +0.5, 1.0 and 2.0 mM silicic acid on hepatic adenylate cyclase (a.c.) activity. Silicic acid at all concentrations enhanced glucagon-stimulated a.c. activity.

This invention pertains to a process for modulating an adenylate cyclase, said process comprising contacting said cyclase with a small, modulating amount of monosilicic acid. In a preferred embodiment, this invention relates to modulation of hormone-stimulated adenylate cyclase systems. This invention comprises the discovery that many adenylate cyclase systems can be modulated with silicic acid. For example, adenylate cyclase systems can be modulated in liver, kidney, thyroid, and bone tissue. For the purpose of this invention, "modulate" means to enhance or inhibit.

Thus, this invention relates to the use of silicic acid to modulate an adenylate cyclase system, particularly such a system in a warm-blooded, vertebrate animal. The silicic acid may be administered per se to the animal being treated. Alternatively, the silicic acid may be produced in vivo by the animal subject from a therapeutic agent which is administered to the animal. The silicic acid may be produced in the gastrointestinal tract, or in the gastrointestinal mucosa, or at any other site of the animal being treated. The silicic acid may be monosilicic acid, or other soluble or suspendable hydrated silicic acid or derivative thereof obtained by polymerization of silicic acid in an aqueous system, e.g. a physiological media such as blood plasma. Salts of such materials, e.g. sodium and potassium salts, are useful as sources of silicic acid.

The concentration of silicic acid species employed in this invention is a small amount, generally up to about the level of saturation of the silicic acid. In general, the concentration can be from about 0.05 to about 2.0 millimolar. Concentrations somewhat outside this range can be used, if desired. For example as indicated above, the concentration can exceed the saturation level; there may be a saturated solution of silicic acid admixed with suspended, small particles (0.1–5.0 microns, for example) of silicic acid suspended in the physiological fluid. Lower concentrations may be suitable at certain sites and levels of enzyme activity to achieve selective, differential effects.

The amount of active agent administered to the animal is selected (to give a concentration within the parameters discussed above) as needed to achieve the desired response.

EXPERIMENTAL METHODS

(a) Enzyme Preparation

Bone Membranes—Harley guinea pigs (550–600 g) were anesthetized with pentobarbital and sacrificed by opening the thoracic cavity; Rude, R. K., *Endocrinology* 113:1348–1355 (1983). The long bones of the upper and lower extremities were rapidly dissected free of adherent muscle and placed in a buffer containing 0.25 mM sucrose, 25 mM tris (hydroxymethyl) aminomethane hydrochloride (Tris HCl), and 7.0 mM (EGTA), pH 7.4 (buffer A) at 4° C. The diaphyseal portions of the bone was isolated and any remaining muscular and connective tissue scraped off. The bone was then split longitudinally and the marrow scraped out. The bone was then crushed into small pieces, washed in buffer A, frozen on dry ice, and then pulverized for 3 minutes in liquid $N_2$ in a Spex freezer/mill (Spex Industries, Inc., Metuchen, N.J.). Further homogenation was carried out for 10–15 seconds in ice cold buffer A with a polytron homogenizer. The homogenate was centrifuged in a Sorvall RC2-B refrigerated centrifuge at 2200 $\times$ g for 10 minutes. The resultant pellet was resuspended in buffer A and recentrifuged at 480 $\times$ g on-off to eliminate heavier particles. The supernatant was then further centrifuged at 2200 $\times$ g for 10 minutes, and the pellet again washed in buffer A and recentrifuged. This final pellet was reconstituted in buffer A, aliquoted into glass tubes and stored at $-70°$ C. until enzyme assay. Immediately prior to assay the membranes were washed in 20 volumes of buffer A and centrifuged at 2200 $\times$ g 4–6 times until the $Ca^{++}$ concentration in the supernatant was less than 4 micromoles as determined by atomic absorption spectrophotometry (Perkin-Elmer 560, Norwal, Conn.). The resultant pellet was then washed twice in 20 volumes of adenylate cyclase assay buffer consisting of 25 mM Tris HCl, 30 mM KCl, 1 mM dithiothreitol (DTT), 0.013 percent (wt/vol) bovine serum albumin (BSA), pH 8.0 at 4° C. before dilution to the desired concentration for use in the assay.

In later experiments a sucrose density fractionation step was added to the membrane preparation. Immediately following the 450 $\times$ g centrifugation, the supernatant was layered over a 15 ml volume of bone buffer containing 60 percent sucrose and centrifuged at 192 $\times$ g for 20 minutes. The membrane fraction which localized at the top of the sucrose layer was collected. It was then washed until free of calcium as described above. This procedure has increased the specific activity of the membrane preparation approximately 2-fold.

(b) Kidney and Thyroid

After sacrifice the kidneys were rapidly removed and replaced in a buffer on 0.25M sucrose, 25 mM Tris-HCl (pH 7.5 at 30C), 1 mM ethylene diamine tetraacetic acid (EDTA), and 1 mM DTT at 4° C. (14). After the renal capsule was removed and fat dissected free, the kidneys were split sagittally and the cortex dissected from the modulla. The renal cortex was then finely minced with a scalpel and homogenized with six strokes of a chilled glass Dounce homogenizer. The homogenate was centrifuged in a Sorvall RC2-B centrifuge at 480 $\times$ g for 10 minutes. The resultant pellet was resuspended in a buffer containing 25 mM Tris HCl (pH 7.5 at 30° C.), 1 mM DTT, 30 mM KCl, and 0.013 percent (wt/vol) BSA at 4° C. and served as a partially purified plasma membrane preparation. Aliquots were placed in glass tubes and stored at $-70°$ C. until enzyme assay. Plasma membranes were also obtained from guinea pig thyroid and liver. The thyroid gland was removed, dissected free from fat tissue, and plasma membranes prepared as described for kidney cortex.

The liver was removed and minced well in a chilled Petri dish. The tissue was homogenized in 0.001 M $NaHCO_3$ (4° C.) in a large Dounce homogenizer (six strokes). Pooled homogenate was washed in 500 ml 0.001M $NaHCO_3$ at 4° C. for 3 minutes. After centrifugation at 1500 $\times$ g for 19 minutes, the pellet was again homogenized in 0.001M $NaHCO_3$, 1 mM EDTA, and 1 mM DTT. The homogenate was then centrifuged at 2200 $\times$ g for 10 minutes. The resultant pellet was washed in reconstitution buffer, centrifuged again at 2200 $\times$ g for min, and aliquots of this pellet were stored at $-70°$ C. until enzyme assay.

(c) Enzyme Assay

Aliquots of membrane suspension, containing 10–50 micrograms protein, were incubated at 30° C. for 15 minutes in the presence of 30 mM KCl, 25 mM Tris-HCl, pH 8.0, 1 mM dithiothreitol, 0.5 mM cyclic AMP, 2.5 uCi $^{32}$P-ATP (Amersham Corp., Arlington Heights, Ill.), 1 mM ATP, and an ATP regenerating system, consisting of 2.5 units of pyruvate kinase and 0.3 mg phosphoenol pyruvate in a total volume of 100 ul. $MgCl_2$ was added to achieve the desired concentration. The amounts of ATP and $MgCl_2$ required to establish the desired concentrations of $Mg^{++}$, and Mg-ATP was determined by computer assisted solution of simultaneous equations describing the relevant multiple equilibria between Mg and ATP. $CaCl_2$ and EGTA have been added to recent experiments. The use of the 0.5 mM EGTA in the reaction mixture serves two purposes: (1) to establish a low medium $Ca^{++}$ concentration, and (2) to generate a calcium and magnesium buffer system in the reaction mixture. The amounts of ATP, $MgCl_2$ required to establish the desired concentrations of $Mg^{++}$, $Ca^{++}$ and Mg-ATP was determined by computer assisted solution of simultaneous equations describing the relevant multiple equilibria between these cations and ATP and EGTA.

Silicic Acid, n-Hydrate, Power, "Baker Analyzed" Reagent was purchased from VWR Scientific and used for addition to the adenylate cyclase assay. The silicic acid was brought up in deionized water to 10X assay concentration and then to final concentration in assay buffer.

Determination of Silicon Concentration

In order to assess the concentration of silicon in the assay system, was determined by use of atomic absorption spectrophotometry utilizing Perkin Elmer 560 spectrophotometer. Silicon, 1000 ppm solution (atomic absorption standard) and Silicon Reference Standard were purchased from VWR Scientific.

Results

The invention comprises the effect of monosilicic acid on basal and hormone-stimulated adenylate cyclase activity in the presence of 4.0 mM Mg and 1 mM Mg-ATP. Monosilicic acid was added at concentrations of 0.5 mM, 1.0 mM, and 2.0 mM. Higher concentrations result in precipitation of silicic acid polymers; Iler, R. K.: The Occurrence Dissolution, and Deposition of Silica, in: The Chemistry of Silica, John Wiley and Sons, New York, page 10. NaF was also included in each assay as a positive control.

Liver Adenylate Cyclase

FIG. 1 shows liver adenylate cyclase in pMole cyclic AMP generated per assay tube. Basal activity was 12.5 pMole cyclic AMP and NaF was 45 pMole cyclic AMP. As noted, 0.5 mM silicic acid had little effect on basal activity however, 2.0 mM silicic acid nearly doubled the activity. Glucagon (Glu) increased basal activity to 17 pMole/tube. The presence of silicic acid at all concentrations markedly enhanced the Glu effect so that Glu + 2.0 mM silicic acid resulted in a greater activity than NaF (52 pMole/cyclic AMP/tube). Table I gives the results obtained.

TABLE I

| Cyclic AMP Generated, pMole/tube | |
|---|---|
| Basal | 13.7 |
| Na F | 45.2 |
| Si, 0.5 mM | 12.1 |
| Si, 1.0 mM | 17.2 |
| Si, 2.0 mM | 22.2 |
| Glucagon | 19.6 |
| Glucagon + Si, 0.5 mM | 36.5 |
| Glucagon + Si, 1.0 mM | 47.5 |
| Glucagon + Si, 2.0 mM | 52.2 |

Kidney Adenylate Cyclase

Figure 2:
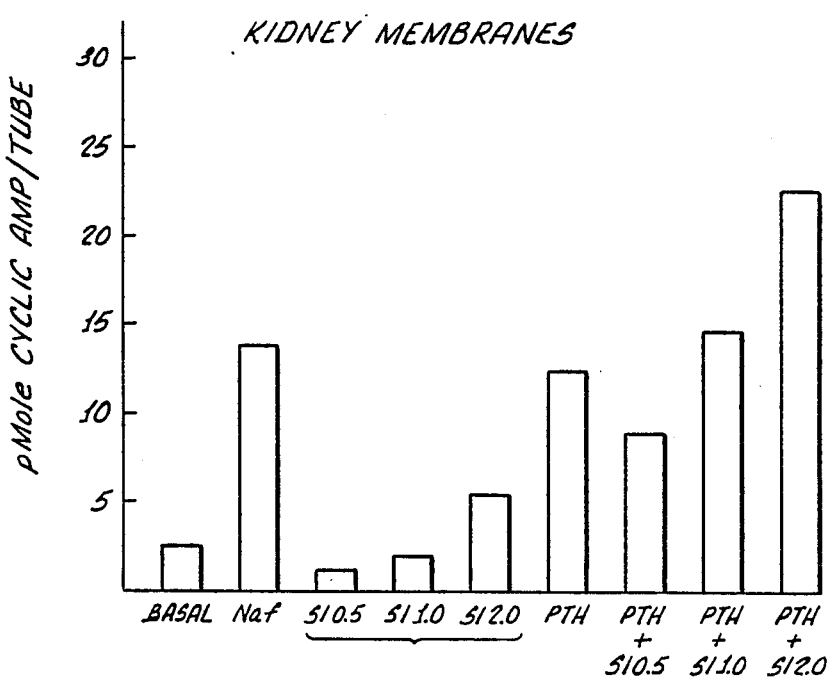
FIG. 2: Effect of NaF, 0.5, 1 0 and 2.0 mM silicic acid, Parathyroid hormone (PTH), and PTH +0.5, 1.0 and 2.0 mM silicic acid on renal a.c. activity. Silicic acid at 0.5 mM slightly decreased a.c. activity but was stimulatory at 2.0 mM. Similarly, 0.5 mM silicic acid decreased PTH-stimulated a.c. activity. However, 1.0 and 2.0 mM silicic acid enhanced the PTH effect.

As shown in FIG. 2, the results were similar to those obtained with liver. Silicic acid, however, at 0.5 mM appeared to inhibit adenylate cyclase activity, however, at 2.0 silicic acid, activity had more than doubled (2.1-5.5 pMole cyclic AMP/tube). Parathyroid hormone (PTH) enhanced adenylate cyclase activity and 0.5 mM silicic acid again appeared to inhibit activity. Silicic acid at 1.0 and 2.0 mM enhanced PTH-stimulated activity to greater than NaF control (23 pMole/cyclic AMP/tube). Table II gives the results obtained.

TABLE II

| Cyclic AMP Generated, pMole/tube | |
|---|---|
| Basal | 2.24 |
| Na F | 14.3 |
| Si, 0.5 mM | 1.15 |
| Si, 1.0 mM | 1.96 |
| Si, 2.0 mM | 5.59 |
| PTH | 13.0 |
| PTH + Si, 0.5 mM | 9.7 |
| PTH + Si, 1.0 mM | 15.5 |
| PTH + Si, 2.0 mM | 23.0 |

Thyroid Adenylate Cyclase

Figure 3:
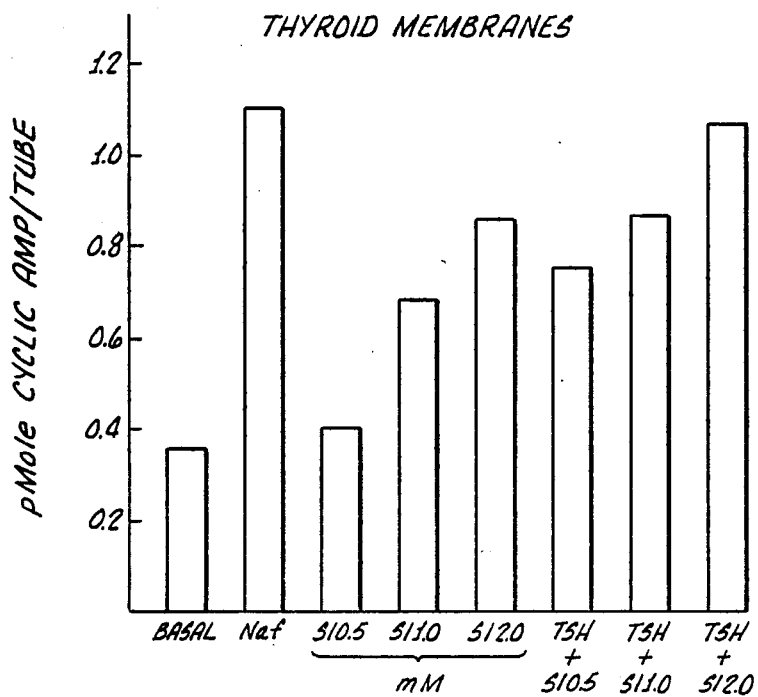
FIG. 3: Effect of NaF, 0.5, 1.0 and 2.0 mM silicic acid, thyroid stimulating hormone (TSH) and TSH + 0.5, 1.0, and 2.0 mM on thyroid a.c. activity. Silicic acid at all concentrations increased a.c. activity. Silicic acid at 1.0 and 2.0 mM also enhanced TSH-stimulated a.c. activity.

Silicic acid at all concentrations enhanced cyclic AMP accumulation under basal condition (FIG. 3) (basal=0.35; 2.0 mM silicic acid=0.86 pMole/cyclic AMP/tube). As with liver and kidney, silicic acid also enhanced the effect of thyroid stimulation hormone (TSH) on adenylate cyclase activity. Table III gives the results obtained.

TABLE III

| Cyclic AMP Generated, pMole/tube | |
|---|---|
| Basal | 0.35 |
| Na F | 1.11 |
| TSH | 0.75 |
| Si, 0.5 mM | 0.40 |
| Si, 1.0 mM | 0.69 |
| Si, 2.0 mM | 0.87 |
| TSH + Si, 0.5 mM | 0.76 |
| TSH + Si, 1.0 mM | 0.87 |
| TSH + Si, 2.0 mM | 1.08 |

Bone Adenylate Cyclase

Figure 4:
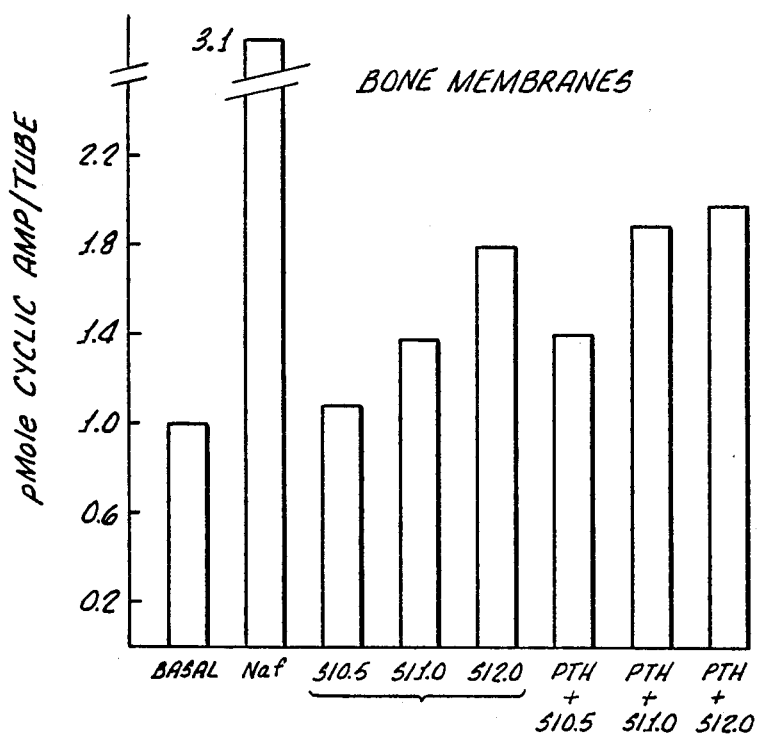
FIG. 4: Effect of NaF, 0.5, 1.0 and 2.0 mM silicic acid, PTH and PTH + 0.5, 1.0 and 2.0 mM silicic acid on skeletal a.c. activity. Silicic acid at all concentrations increased a.c. activity. Additionally, all concentrations of silicic acid enhanced the effect of PTH-stimulated a.c. activity.

As shown in FIG. 4, silicic acid at all concentrations increased basal adenylate cyclase activity (1.0 to 1.8 pMole cyclic AMP/tube at 2.0 mM silicic acid). Additionally, all doses of silicic acid enhanced the effect of PTH on adenylate cyclase activity (1.4 pMole, PTH without silicic acid; 2.0 pMole cyclic AMP, PTH + 2.0 mM silicic acid).

Effect of Silicon in the Presence of EGTA

Figure 5A:
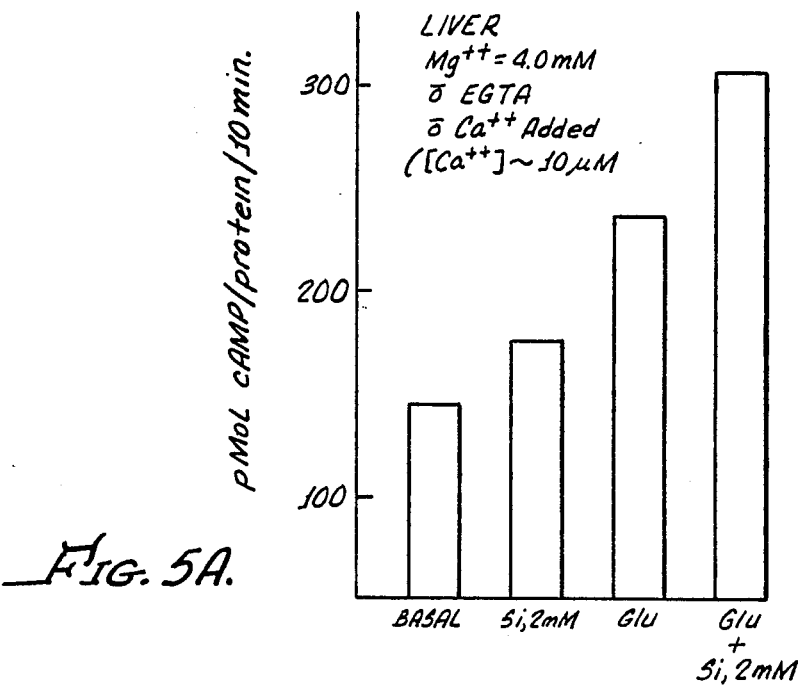
FIG. 5: Comparison of the effect of 2.0 mM silicic acid on hepatic adenylate cyclase activity in the absence (panel A) or presence (panel B) of 0.5 mM ethylene glycol-0,0'-bis (2-aminoethyl)-N,N,N',N'-tetraacetic acid (EGTA). Estimated $Ca++$ is 10 micromoles in panel A and calculated $Ca_{++}=0.2$ micromoles in panel B. Silicic acid increased basal and glucagon stimulated activity as shown in panel A. The addition of EGTA resulted in marked enhancement of both basal and glucagon stimulated adenylate cyclase activity. Under these conditions 2.0 mM silicic acid had no effect.
Figure 5B:
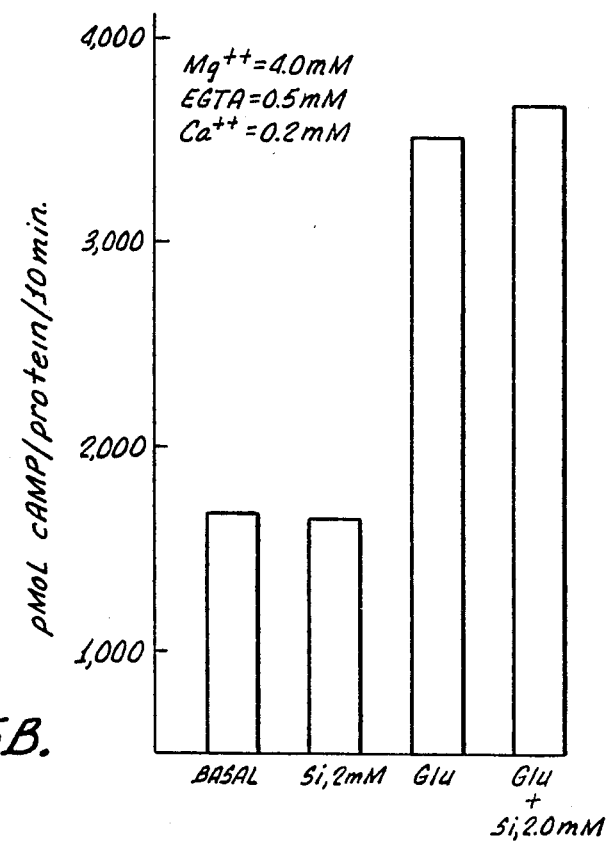
Figure 6A:
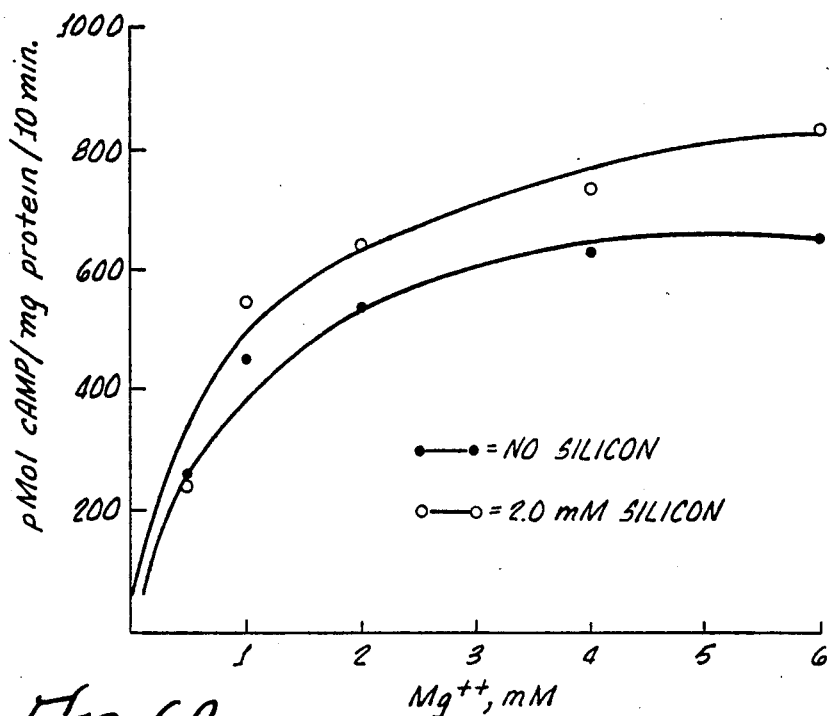
FIG. 6: Effect of $Mg^{++}$ on skeletal adenylate cyclase in the presence (o----o) and absence (.----.) of 2.0 mM silicic acid is shown in panel A. Double reciprocal plots of the data in panel A is shown in panel B. Silicic acid caused an increase in Vmax but little change in KaMg.
Figure 6B:
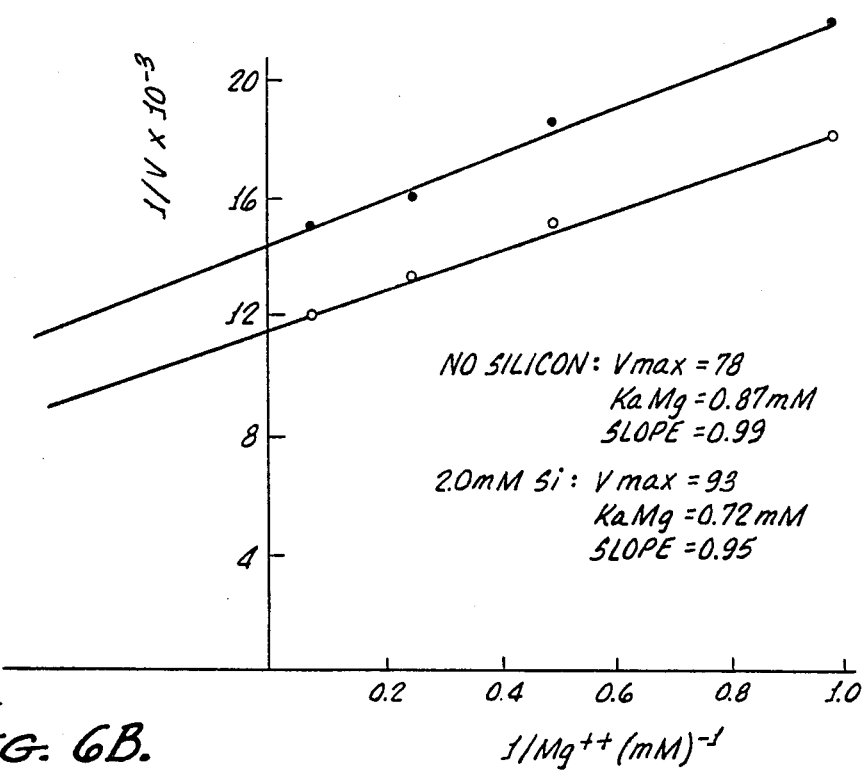
Figure 7:
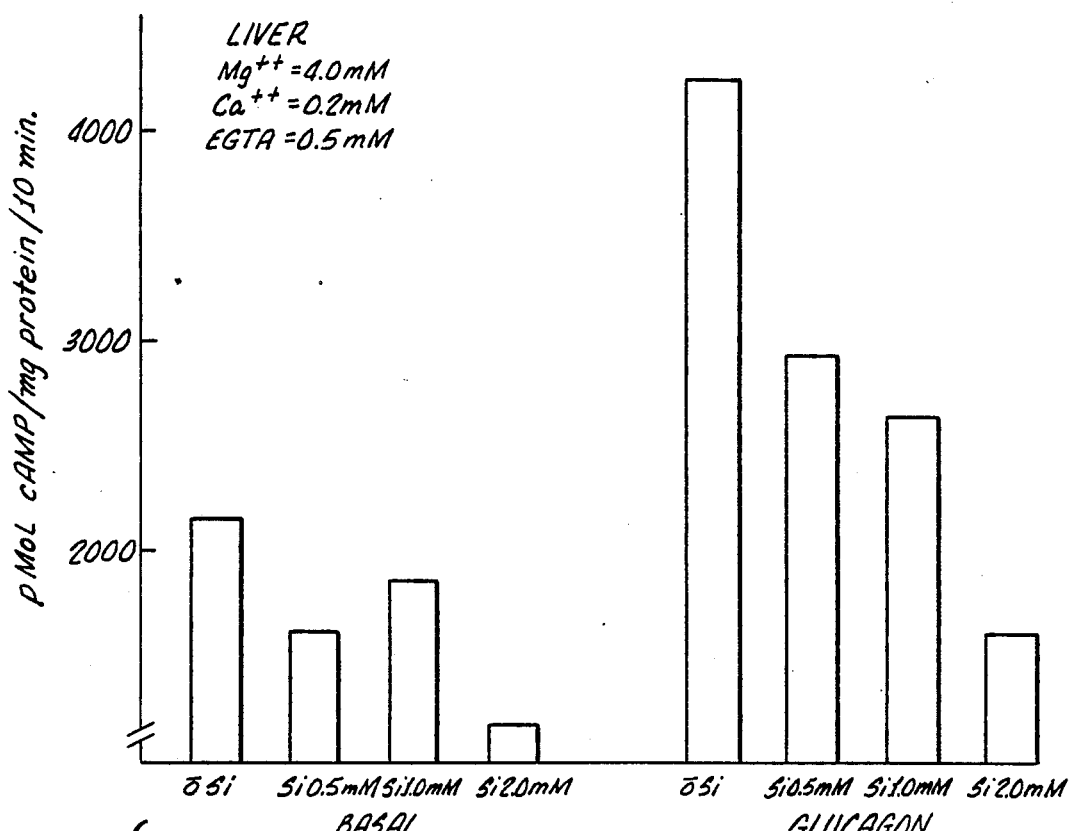
FIG. 7: Inhibition of adenylate cyclase activity by $Ca^{++}$, 0.1 micromoles to 1 mM in the presence (o-----o) and absence (x----x) of 2.0 mM silicic acid. Silicic acid was not observed to prevent the ability of $Ca^{++}$ to inhibit enzyme activity.

Since one potential mechanism for silicon to affect adenylate cyclase is via binding divalent cations, a comparison was made of the effect in a buffer system as before, in which the estimated $Ca^{++}$ concentration is approximately 10 micromoles and a system including 0.5 mM EGTA with a $Ca^{++}$ concentration of 0.2 micromoles. As shown in the left panel in FIG. 5, 2 mM silicic acid again increased adenylate cyclase activity above basal and glucagon stimulation in liver cell membranes. In the presence of EGTA, basal and glucagon activity was markedly increased and 2 mM silicic acid had no additional effect. These data suggested that silicon may bind $Ca^{++}$ and decrease the inhibitory action of $Ca^{++}$. If this were true, double reciprocal plots of $Mg^{++}$ activation of adenylate cyclase with and without silicic acid should have the appearance of competitive inhibition. As seen in FIG. 6, however, this was not true and suggested that the effect of silicic acid is not solely mediated by binding to $Ca^{++}$. This is also supported by the finding that silicic acid did not prevent $Ca^{++}$ inhibition of adenylate cyclase as shown in FIG. 7.

Figure 8:
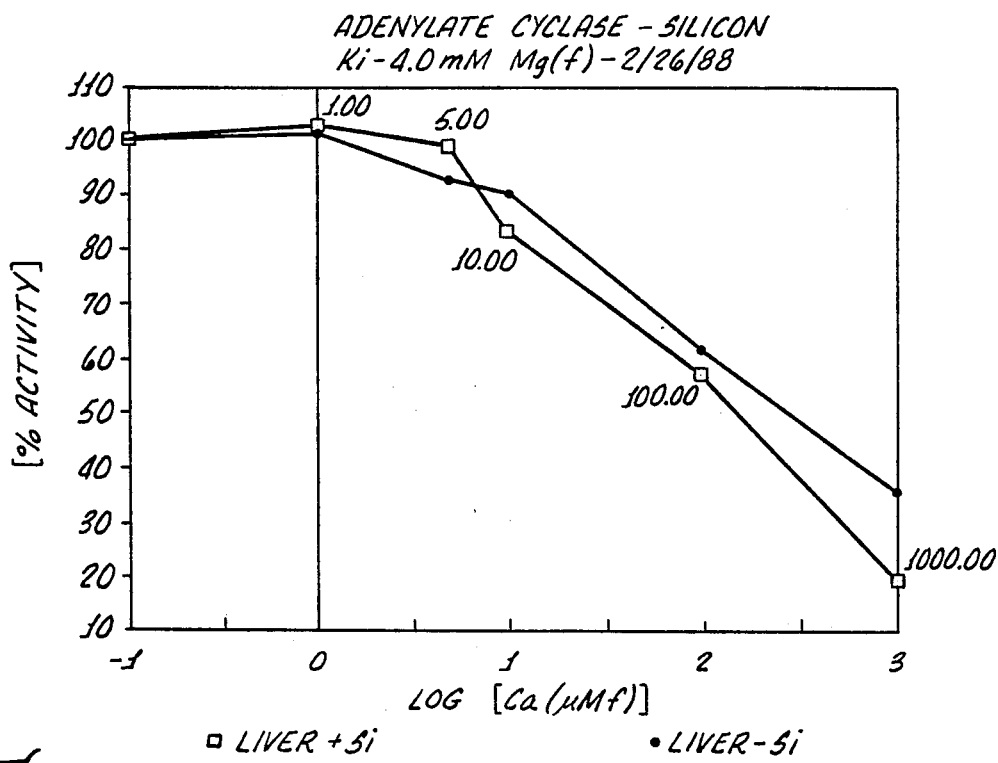
FIG. 8: Effect of 0.5, 1.0 and 2.0 mM silicic acid on basal and glucagon stimulated liver cell adenylate cyclase activity in the presence of 0.5 mM EGTA. Increasing silicic acid concentrations progressively inhibited enzyme activity.

In other experiments, silicic acid concentration in the buffer used was determined by atomic absorption spectrophotometry. A dose dependent response to silicic acid was assessed in liver cell membranes as shown in FIG. 8. As seen, there was a progressive inhibition of adenylate cyclase activity from basal activity to silicic acid concentrations of 2.0 mM in the presence of 0.5 mM EGTA and 0.2 micromoles $Ca^{++}$.

Discussion

The results of these experiments demonstrate that silicic acid will enhance basal and hormone-stimulated adenylate cyclase activity. This effect appears to be a general one in as much as this augmentation has occurred in all tissues studied.

The mechanism(s) responsible for this effect is (are) unclear. The lack of effect of silicic acid in the presence of EGTA suggests that silicic acid may merely be acting via binding ionized $Ca^{++}$ and thereby increasing adenylate cyclase activity by removing the inhibitory action of $Ca^{++}$. Since $Ca^{++}$ is an important intracellular second messenger and silicic acid has been found within the cell, this is a possible mechanism of the effect of silicic acid *in vivo*. The lack of finding competitive inhibition in FIG. 6 as well as the lack of effect of silicic acid on impairing $Ca^{++}$ inhibition in FIG. 7 indicates that more is involved. Silicic acid could also bind $Mg^{++}$ and cause a reduction in adenylate cyclase activity. This could explain the finding in FIG. 8 where $Ca^{++}$ was low (0.2 micromoles) and silicic acid caused inhibition of activity. However, monosilicic acid is a very weak acid, it is thought to only interact with metal ions at pH levels below the level at which hydroxide precipitation occurs which would exclude $Ca^{++}$ and $Mg^{++}$ at a physiological pH.

Other potential mechanisms also exist. Monosilicic acid may either influence $Mg^{++}$ activation or $Ca^{++}$ inhibition of N protein(s) or the affinity of these divalent cations for the N protein. Additionally, silicic acid could directly cause activation of Ns or inhibition of Ni activity. Other potential mechanisms include a decrease in K-activation by hormone or direct enhancement of catalytic subunit activity.

Although the clinical significance of these findings remain to be elucidated, the above results suggest many uses of silicic acid in human and veterinary medicine. More specifically, the results indicate that silicic acid can be used to modulate hormone response. For example, the results with glucagon suggest that silicic acid sources can be used to regulate blood sugar levels in patients wherein the effect of glucagon is lower than desired.

Among the states which may be modified by treatment with silicic acid, or a compound supplying silicic acid, are osteopenia, hypoglycemia, hypocalcemia, and the like, all responses being mediated by a particular hormone/adenylate cyclase/tissue system. For purposes of example, an embodiment of this invention of particular interest is the treatment of osteoporosis with silicic acid, or a compound which supplies the acid. Other conditions such as hypertension/hypotension, which are affected by neurotransmitters of the $\beta$-adrenergic blocker/ $\beta$-adrenergic agonist classes, are targets for therapy by silicate supplying materials, since these conditions are also controlled by particular adenylate cyclase systems. In concept, any process mediated by cyclic AMP is a target for silicate treatment.

Since this study indicates that silicic acid affects adenylate cyclase activity, and in this manner exerts an effect on skeletal growth and/or bone mineralization, it is suggested that silicic acid can be used to prevent, treat, or delay the onset of calcium-related bone disease, or to increase the strength of bone in a human or animal subject having a bone strength less than desired. Thus, the results reported above indicate that silicic acid can be used to treat osteopenia in vertebrate animals such as man, and domestic animals of commercial importance including canine, feline, bovine, and ovine species, and swine. In humans, it is suggested that silicic acid can be used to treat (a) post-menopausal osteoporosis, (b) osteoporosis produced by steroid therapy, and (c) bone mineralization loss due to prolonged bed-ridden therapy, or prolonged space travel.

A skilled practitioner aware of the above detailed description can make many modifications of the disclosed invention without departing from the scope or spirit of the appended claims.

We claim:

1. A process for modulating the enzymatic activity of an adenylate cyclase, said process comprising contacting said cyclase with a modulating amount of silicic acid said modulating amount being no more than about the level of saturation of silicic acid.

2. The process of claim 1, wherein said modulating amount is a concentration of from about 0.05 to about 2.0 millimolar.

3. The process of claim 1, wherein said silicic acid is monosilicic acid.

4. The process of claim 1, wherein said cyclase is liver adenylate cyclase.

5. The process of claim 1, wherein said cyclase is kidney adenylate cyclase.

6. The process of claim 1, wherein said cyclase is thyroid adenylate cyclase.

7. The process of claim 1, wherein said cyclase is bone adenylate cyclase.

* * * * *

UNITED STATES PATENT AND TRADEMARK OFFICE
CERTIFICATE OF CORRECTION

PATENT NO. : 4,954,448

DATED : September 4, 1990

INVENTOR(S) : KARL E. WIEGAND and ROBERT K. RUDE

It is certified that error appears in the above—identified patent and that said Letters Patent is hereby corrected as shown below:

On the title page, item [73], the Assigneee is corrected to read:

ETHYL CORPORATION, RICHMOND, VIRGINIA

Signed and Sealed this

Nineteenth Day of May, 1992

Attest:

DOUGLAS B. COMER

*Attesting Officer*  *Acting Commissioner of Patents and Trademarks*